United States Patent
Gartner et al.

(10) Patent No.: US 6,323,252 B1
(45) Date of Patent: Nov. 27, 2001

(54) SUPERABSORBENT POLYMERS HAVING IMPROVED PROCESSABILITY

(75) Inventors: Herbert A. Gartner, Baden-Baden (DE); Thomas L. Staples, Midland, MI (US); Michael A. Fialkowski, Burnsville, MN (US)

(73) Assignee: The Dow Chemical Company, Midland, MI (US)

( * ) Notice: Subject to any disclaimer, the term of this patent is extended or adjusted under 35 U.S.C. 154(b) by 0 days.

(21) Appl. No.: 09/403,812

(22) PCT Filed: Mar. 5, 1998

(86) PCT No.: PCT/US98/07963
§ 371 Date: Jan. 10, 2000
§ 102(e) Date: Jan. 10, 2000

(87) PCT Pub. No.: WO98/49221
PCT Pub. Date: Nov. 5, 1998

Related U.S. Application Data
(60) Provisional application No. 60/044,417, filed on Apr. 29, 1997.

(51) Int. Cl.[7] .................................................... C08J 9/28
(52) U.S. Cl. .............................. 521/149; 521/61; 521/63; 521/64; 521/123; 526/317.1; 526/318.1; 526/318.2
(58) Field of Search .............................. 521/149, 61, 63, 521/64, 123; 526/317.1, 318.1, 318.2

(56) References Cited

U.S. PATENT DOCUMENTS

| | | |
|---|---|---|
| 3,926,891 | 12/1975 | Gross et al. . |
| 3,935,099 | 1/1976 | Weaver et al. . |
| 3,997,484 | 12/1976 | Weaver et al. . |
| 4,043,952 | 8/1977 | Ganslaw et al. . |
| 4,076,663 | 2/1978 | Masuda et al. . |
| 4,090,013 | 5/1978 | Ganslaw et al. . |
| 4,093,776 | 6/1978 | Aoki et al. . |
| 4,190,562 | 2/1980 | Westerman . |
| 4,340,706 | 7/1982 | Obayashi et al. . |
| 4,446,261 | 5/1984 | Yamasaki et al. . |
| 4,459,396 | 7/1984 | Yamasaki et al. . |
| 4,683,274 | 7/1987 | Nakamura et al. . |
| 4,708,997 | 11/1987 | Stanley et al. . |
| 4,833,222 | 5/1989 | Siddall et al. ........................ 526/200 |
| 5,002,986 | 3/1991 | Fujiura et al. ......................... 524/47 |
| 5,385,983 | 1/1995 | Graham ............................. 525/330.1 |

FOREIGN PATENT DOCUMENTS

| | | |
|---|---|---|
| 1993-127054 | 12/1993 | (DE) . |
| 309187 | 3/1989 | (EP) . |
| 605215 | 7/1994 | (EP) . |
| 92/20727 | 11/1992 | (WO) . |
| 93/05080 | 3/1993 | (WO) . |
| 94/22940 | 10/1994 | (WO) . |
| 95/05856 | 3/1995 | (WO) . |

*Primary Examiner*—John M. Cooney, Jr.

(57) ABSTRACT

A composition comprising aqueous fluid absorbent polymer particles which have been heat-treated at temperatures greater than 170° C. for more than 10 minutes, wherein the composition has been remoisturized, after the heat-treatment, with an aqueous additive solution, in the absence of an organic solvent or water-insoluble, non-swellable powder, and comprises 1 to 10 percent by weight, based on the total weight of the composition, water and wherein the composition is characterized by the ability to absorb at least 20 grams of a 0.9 weight percent aqueous saline solution under a pressure of 0.3 psi (21,000 dynes/cm$^2$), that is, a 60 minute 0.3 psi (21,000 dynes/cm$^2$) AUL greater than 20 grams/gram. A process for preparing such a composition.

22 Claims, No Drawings

SUPERABSORBENT POLYMERS HAVING IMPROVED PROCESSABILITY

This application claims benefit of Provisional Application Ser. No. 60/044,417 filed Apr. 29, 1997.

In the gel polymerization of water-swellable polymers, monomers are polymerized in aqueous solution. Certain additives, such as cross-linking agents, may be incorporated into the monomer mixture. The product of the polymerization process is typically dried and subjected to mechanical means of particle size reduction and classification including chopping, grinding, and sieving. If desired, the dried superabsorbent polymer particles may be further surface modified and/or heat treated. Such post-heat-treatment leads to an almost entirely dry product with a strong tendency to build up static electricity during handling, which can, in turn, cause processing difficulties. Such static electricity build-up is extremely undesirable since it negatively influences the accuracy of superabsorbent polymer dosing and its distribution in personal care articles, such as diapers or sanitary napkins. Certain treatments are then required to minimize the static electricity build-up during the handling of the superabsorbent polymer (SAP) thereby increasing the electric conductivity of the surface of the SAP particles. Such treatments include, for example, addition of water, or polyethylene glycols.

It is known that more plasticized surfaces are less friable. Friability can cause property degradation and dust production in the polymer. It is also known that water can be a plasticizer for superabsorbent polymers. However, one major problem associated with the addition of water is the tendency of the SAP particles to swell on the surface and become sticky. As increasing amounts of water are added, the superabsorbent polymer becomes more cohesive and less processable.

In the past, the production of SAP did not comprise a post-heating treatment, thus, the addition of water to the polymerized and dried SAP was not required since the SAP thus prepared still contained moisture. However, it has been known to add aqueous solutions to the superabsorbent polymers in order to enhance certain properties thereof. The addition of such aqueous solutions, for example, to add surface post-cross-linkers or other additives or processing agents, is typically carried out in the presence of organic solvents, or anti-agglomerating agents, in order to prevent or minimize agglomeration caused by the water, which otherwise would occur.

European Patent Application 605,215 discloses a method for treating an absorbent resin by adding to the absorbent resin powder a substance capable of reacting with the residual monomer in the absorbent resin powder, thereby forming an absorbent resin composition having a water content in the range of 10 to 70 percent by weight and heat-treating the absorbent resin composition at a temperature in the range of 100° C. to 200° C. for not less than 10 minutes while retaining the water content of the absorbent resin within 20 percent. An alternative method comprises the addition to the absorbent resin powder of a substance capable of reacting with the residual monomer in the absorbent resin powder, thereby forming an absorbent resin composition having a water content in the range of 25 to 55 percent by weight and heat-treatment of the absorbent resin composition at a temperature in the range of 120° C. to 200° C. for a period of not less than 10 minutes while retaining the water content of the absorbent resin in the range mentioned above, and then drying the absorbent resin composition at a temperature not exceeding 120° C.

European Patent Application 309,187 discloses absorbent materials, such as cross-linked, water-soluble and water-swellable particulate polymers, which are immobilized and safely handled by adding an aqueous liquid, such as water or saline in amounts sufficient to form hydrates in which the water comprises from 20 percent to 80 percent by weight of the total hydrate.

U.S. Pat. No. 4,043,952 discloses a process for surface treating a water-absorbent composition to improve its aqueous dispersibility by a) forming a dispersion comprising a water-absorbent composition based on anionic polyelectrolyte, polyvalent cations of at least one metal, and a dispersing medium in which said composition is substantially insoluble; b) maintaining said dispersion at a temperature of −40° C. to +150° C. for a period of time sufficient for said cations to ionically complex the outer surface of said composition exposed to said dispersing medium; and c) removing said dispersing medium.

However, the surface treatment techniques of the state of the art, especially those not employing any anti-agglomerating agent, still present a major drawback of agglomerating the polymer particles, which agglomeration is substantially irreversible. Thus, it would be highly desirable to find means of preventing or minimizing undesirable and irreversible agglomeration without the need of using organic solvents, or water-insoluble, non-swellable powders as anti-agglomerating agents. Therefore, industry would find great advantage in improved aqueous fluid absorbent polymers which possesses reduced tendencies to build up static electricity and to generate dust, sufficient fine dust binding capability without causing undesirable agglomeration of the polymer particles in the surface treatment process. Industry would further find advantage in a process for distributing more homogeneously additives on the surface of superabsorbent polymers.

Accordingly, the present invention provides a composition comprising aqueous fluid absorbent polymer particles which have been heat-treated at temperatures greater than 170° C. for more than 10 minutes, wherein the composition has been remoisturized, after the heat-treatment, with an aqueous additive solution, in the absence of an organic solvent or water-insoluble, non-swellable powders, and comprises up to 10 percent by weight, based on the total weight of the composition, water and wherein the composition is characterized by the ability to absorb at least 20 grams of a 0.9 weight percent aqueous saline solution under a pressure of 0.3 psi (21,000 dynes/cm$^2$), that is, a 60 minute 0.3 psi (21,000 dynes/cm$^2$) AUL greater than 20 grams/gram as measured in accordance with the Absorption Under Load Test set forth in U.S. Pat. No. 5,147,343.

The present invention further provides a process comprising:

(a) preparing a water-swellable hydrogel by a gel polymerization process;

(b) drying and sizing the hydrogel to form a composition comprising dried and sized particles, the composition comprising particles having a particle size distribution of 50 to 1500 microns;

(c) heat-treatment; and (d) contacting the composition with an aqueous additive solution in the absence of an organic solvent or water-insoluble inorganic powders, wherein the composition is characterized by a 60 minute 0.3 psi (21,000 dynes/cm$^2$) AUL greater than 20 grams/gram.

Yet another objective of the present invention is a process comprising:

(a) preparing a water-swellable hydrogel by a gel polymerization process;

(b) drying and sizing the hydrogel to form a composition comprising dried and sized particles, the composition comprising particles having a particle size distribution of 50 to 1500 microns;

(c) contacting the composition with an aqueous additive solution in the absence of an organic solvent or water-insoluble inorganic powders, wherein the composition is characterized by a 60 minute 0.3 psi (21,000 dynes/$cm^2$) AUL greater than 20 grams/gram;

(d) drying an/or heat-treating the composition; and, optionally, (e) remoisturization of the heat-treated SAP so that the resultant SAP contains up to 10 percent of water.

Surprisingly, it has been found that the remoisturized polymer particles of the present invention are more homogeneously moisturized to the desired level, with substantially reduced tendency for irreversible agglomeration during the process of remoisturization without sacrificing other physical and/or chemical properties. In view of the reduced tendency for irreversible agglomeration, the remoisturized polymer particles of the present invention exhibit reduced static electricity build-up. Furthermore, the process of the present invention provides remoisturized polymer particles having additives distributed more homogeneously throughout their surface.

Another objective of the present invention is to provide a surface treated superabsorbent polymer wherein the polymer has been contacted with an additive solution before the heat-treatment. The polymer treated with an additive solution according to the present invention will exhibit a more homogeneous distribution of cross-linkers or other surface treatment additives.

"Irreversible agglomeration" as used herein means that the agglomerates require a further grinding to reduce their particle size to a desired range, such as for example, 100 to 800 microns ($\mu$m). Small shear forces as they occur in further processing, such as sieving, and conveying, are not strong enough to disintegrate the agglomerates.

"Undesirable agglomeration" as used herein means adherence of two or more SAP particles to each other to form larger particles (greater than 800 $\mu$m) which may disintegrate to the original particles by the application of adequate shear.

"Water-soluble" as used herein means a substance that is substantially soluble in water, that is, it turns from solid to solution upon contact with sufficient aqueous solution.

"Water-swellable" as used herein means the SAP powder particles are capable of absorbing water or aqueous fluids and thereby increasing their original volume many times, such as at least 10 times, more preferably at least 20 times.

The additives useful in the aqueous additive solution of the present invention include, for example, salts of mono- and selected multivalent metal ions. Suitable metal ions include sodium, potassium, or aluminum ions. Other suitable additives include moderately water-soluble organic substances having a viscosity ranging between 200 to 300 centistokes at 25° C., such as, for example, propoxylated polyols (commercially available under the Trademark VORANOL from The Dow Chemical Company), described in WO94/22940. The propoxylated polyols are particularly suitable to further bind the fine dust of the final SAP product. The amount of aqueous additive solution used in the present invention depends largely on the desired moisturization level of the superabsorbent polymer, type of additive employed and on the product.

If a monovalent salt, such as NaCl or KCl, is employed, the salt is preferably added at a concentration that allows the addition of water to the superabsorbent polymer with minimal undesired or irreversible agglomeration. Typically, the amount of monovalent salt added varies from 0.05 to 5 percent, based on superabsorbent polymer. The salt is preferably added in the form of an aqueous solution having a salt concentration of from 1 to 40 percent, more preferably from 10 to 30 percent, and most preferably 20 percent. The maximum concentration of the monovalent salt is, however, limited by its solubility in the amount of water to be added. If trivalent salts are employed, the concentration is desirably at a level which sufficiently prevents undesired or irreversible agglomeration during the remoisturization process. The maximum concentration of the trivalent salt is limited by its tendency to further cross-link the superabsorbent polymer and, hence, reduce the absorption capacity of the superabsorbent polymer. Therefore, amounts of 500 to 5,000, preferably 1,000 to 2,500 parts per million (ppm) of the trivalent cation, based on the total weight of SAP, are employed.

Due to their detrimental effects concerning AUL performance, divalent cations are not used in this invention. Divalent salts have been found to reduce the swelling capacity of superabsorbents and are, in general, to be avoided.

The water-swellable or lightly cross-linked hydrophilic polymers that are suitably used in the present invention can be any of the known hydrophilic polymers which are capable of absorbing large quantities of fluids. In particular, water-absorbent polymers useful in this invention are water-absorbent polymers which contain carboxyl moieties. Preferably, at least about 0.01 equivalent of carboxyl groups are present per 100 grams of the water-absorbent resin.

Among preferred carboxyl-containing water absorbent polymers are hydrolyzates of starch-acrylonitrile graft copolymers, partially neutralized products of starch-acrylic acid graft copolymers, saponification products of vinyl acetate acrylic ester copolymers, hydrolyzates of acrylonitrile copolymers, cross-linked products of hydrolyzates of acrylonitrile copolymers, cross-linked products of saponified alkylacrylate polymers or copolymers, hydrolyzates of acrylamide copolymers, cross-linked products of hydrolyzates of acrylamide copolymers, partially neutralized products of polyacrylic acids and cross-linked products of partially neutralized polyacrylic acids.

Examples of some suitable polymers and processes for preparing them are disclosed in U.S. Pat. Nos. 3,997,484; 3,926,891; 3,935,099; 4,090,013; 4,093,776; 4,340,706; 4,446,261; 4,683,274; 4,459,396; 4,708,997; 4,076,663; and 4,190,562. Such hydrophilic polymers are prepared from water-soluble $\alpha,\beta$-ethylenically unsaturated monomers, such as monocarboxylic acids, polycarboxylic acids, acrylamide and their derivatives.

Suitable $\alpha,\beta$-ethylenically unsaturated monomers include, for example, acrylic acid, methacrylic acid or esters thereof, crotonic acid, isocrotonic acid and alkali metal salts and ammonium salts thereof; maleic acid, fumaric acid, itaconic acid, acrylamide, methacrylamide and 2-acrylamido-2-methyl-1-propane sulfonic acid and its salts. The preferred monomers include acrylic acid and methacrylic acid and their respective salt forms such as alkali metal or ammonium salts.

For the preparation of the feed polymers, the water-soluble monomer mixture useful in the present invention may be used in amounts ranging from 10 percent to 80 percent by weight based on the total weight of the aqueous monomer mixture solution. Preferably, the amount ranges from 20 percent to 60 percent based on the total weight of the aqueous monomer mixture solution.

Optionally, minor amounts of other water-soluble, unsaturated monomers, such as alkyl esters of the acid monomers, for example, methyl acrylate or methyl methacrylate may be present. In addition, certain grafting polymers, such as, for example, polyvinyl alcohol, starch and water-soluble or swellable cellulose ethers may be employed to prepare products having superior properties. Such grafting polymers, when employed, are used in amounts up to 10 weight percent based on the $\alpha,\beta$-ethylenically unsaturated monomer. Further, it may be advantageous to include a chelating agent to remove trace metals from solution, for example, when a metal reaction vessel is employed. One such chelating agent is VERSENEX V-80 (Trademark of The Dow Chemical Company), an aqueous solution of the pentasodium salt of diethylenetriamine pentacetic acid. Such chelating agents, when employed, are generally used in amounts between 100 and 2000 ppm based on the $\alpha,\beta$-ethylenically unsaturated monomer.

It is desirable to obtain a level of conversion of monomer to polymer of at least about 95 percent. The polymerization may be carried out using acid monomers that are not neutralized or that have been neutralized or partially neutralized prior to the polymerization. Neutralization is conveniently achieved by contacting the aqueous monomer with an amount of basic material sufficient to neutralize between 20 and 95 percent of the acid groups present in the acid monomers. Preferably, the amount of basic material will be sufficient to neutralize between 40 percent and 85 percent, and most preferably between 55 percent and 75 percent of the acid groups present in the acid monomers. When neutralizing the monomer solution, it is important to control the neutralization conditions so that the heat of neutralization does not cause the premature polymerization of the monomer mixture. The neutralization is advantageously carried out at temperatures below 40° C., preferably at temperatures below 35° C.

Compounds which are useful to neutralize the acid groups of the monomer are typically those which will sufficiently neutralize the acid groups without having a detrimental effect on the polymerization process. Such compounds include alkali metal hydroxides, and alkali metal carbonates and bicarbonates. Preferably, the material used to neutralize the monomer is sodium or potassium hydroxide or carbonate. In determining the desired degree of neutralization, care must be taken to ensure that the pH of the resulting cross-linked absorbent polymer, which will be contacted with or dispersed in an aqueous fluid to be absorbed, is maintained in a range appropriate for the applications for which the polymer is intended. Alternatively, the polymerization may be carried out employing unneutralized monomers and thereafter neutralizing, as is known in the art.

Conveniently, a conventional vinyl addition polymerization initiator is used in the polymerization of the water-soluble monomers and the cross-linking agent. A free radical polymerization initiator which is sufficiently soluble in the monomer solution to initiate polymerization is preferred. For example, water-soluble persulfates such as potassium persulfate, ammonium persulfate, sodium persulfate, and other alkali-metal persulfates, hydrogen peroxide and water soluble azo-compounds such as 2,2'-azobis (2-amidinopropane.HCl) may be used. Some of these initiators, such as hydrogen peroxide or sodium persulfate, can be combined with reducing substances such as sulfites, amines or ascorbic acid to form known redox-type initiators. The total amount of initiators used may range from 0.01 to 1.0 weight percent, preferably 0.01 to 0.5 weight percent, based on the total weight of $\alpha,\beta$-ethylenically unsaturated monomer reactants.

The water-absorbent resin will preferably be lightly cross-linked to render it water-insoluble. The desired cross-linked structure may be obtained by the copolymerization of the selected water-soluble monomer and a cross-linking agent possessing at least two polymerizable double bonds in the molecular unit. The cross-linking agent is present in an amount effective to cross-link the water-soluble polymer. The preferred amount of cross-linking agent is determined by the desired degree of absorption capacity and the desired strength to retain the absorbed fluid, that is, the desired absorption under load (AUL). Typically, the cross-linking agent is used in amounts ranging from 0.0005 to 5 parts by weight per 100 parts by weight of $\alpha,\beta$-ethylenically unsaturated monomer used. More preferably, the amount ranges from 0.1 to 1 part by weight per 100 parts by weight of the $\alpha,\beta$-ethylenically unsaturated monomer. If an amount over 5 parts by weight of cross-linking agent per 100 parts is used, the resulting polymer has too high a cross-linking density and exhibits a reduced absorption capacity and increased strength to retain the absorbed fluid. If the cross-linking agent is used in an amount less than 0.0005 part by weight per 100 parts, the polymer has too low a cross-linking density, and when contacted with the fluid to be absorbed becomes sticky, water-soluble to a high degree, and exhibits a low absorption performance, particularly under load.

While the cross-linking agent will typically be soluble in the aqueous solution of the $\alpha,\beta$-ethylenically unsaturated monomer, the cross-linking agent may be merely dispersible in such a solution, and may need the addition of a dispersing agent in order to assure homogeneous distribution of the cross-linker in the monomer solution. The use of such dispersing agents is disclosed in U.S. Pat. No. 4,833,222, the relevant portions of which are incorporated herein by reference. Suitable dispersing agents include carboxymethyl cellulose suspending aids, methyl cellulose, hydroxypropyl cellulose, and polyvinyl alcohol. Such dispersing agents are typically provided at a concentration between 0.005 and 0.1 weight percent, based on the total weight of ethylenically unsaturated monomer reactants.

Typical cross-linking agents include monomers having in one molecule 2 to 4 groups selected from the group consisting of $CH_2=CHCO-$, $CH_2=C(CH3)CO-$ and $CH_2=CHCH_2-$. Exemplary cross-linking agents are diacrylates and dimethacrylates of ethylene glycol, diethylene glycol, triethylene glycol, propylene glycol, 1,4-butanediol, 1,5-pentanediol, 1,6-hexanediol, neopentyl glycol, trimethylolpropane and pentaerythritol; triacrylates and trimethacrylates of trimethylolpropane and pentaerythritol; ethoxylated and highly ethoxylated trimethylolpropane triacrylate; tetracrylate and tetramethacrylate of pentaerythritol; and tetrallyloxyethane.

"Highly ethoxylated", as used herein means a cross-linker molecule possessing, at least 4 ethylene oxide units between two copolymerizable double bonds in the chain.

As noted in WO 93/05080, a certain class of cross-linking agents yields particularly preferred absorptive properties. Such preferred cross-linking agents include methylenebisacrylamide, bis(acryl-amido)acetic acid and its salts, allyl acrylate, allyl methacrylate, and esters or amides having both a vinyl and an allyl functionality. Highly ethoxylated trimethylol propane triacrylate is a particularly preferred cross-linking agent.

In a preferred embodiment for making polymers useful in the practice of this invention, an aqueous solution of the $\alpha,\beta$-ethylenically unsaturated monomer in the partially neutralized form, the cross-linking agent, the initiator and a grafting polymer substrate, if desired, is prepared.

The polymerization of the mixture may be initiated by elevating the temperature of the mixture containing the initiator or by using a redox-type initiator as described above. Generally, the temperature at which polymerization will begin ranges from 20° C. to 45° C. The temperature at which the polymerization is carried out is highly dependent on the type of monomers used and the specific initiator system employed. Preferably, the maximum temperature of polymerization ranges from 50° C. to 100° C., most preferably from 60° C. to 100° C. The method by which the temperature of the polymerization is controlled is not critical so long as sufficient cooling is present to remove the excess heat which is generated during the polymerization.

The resultant polymer is typically pre-sized and dried using means well-known in the art. Suitable drying means include fluidized bed dryers, rotary dryers, forced-air ovens, and through circulation band dryers. In some instances, drying will occur in two or more stages. In two-stage drying, the pre-sized polymer particles are partially dried in the first stage, for example, the pre-sized polymer particles are dried to less than about 10 percent moisture level, preferably about a 5 percent moisture level. During initial drying, the pre-sized particles typically fuse together into sheets. Following the completion of drying, the polymer is more completely sized to form particles having an average diameter less than 0.8 mm with a mean diameter between 300 and 500 microns. During such sizing, dust, characterized by particle sizes may result, that is, particle sizes less than or equal to 100 $\mu$m.

To improve absorptive properties, the dried particles may be heat-treated in accordance with the procedures set forth in WO 93/05680, and/or PCT Application PCT/US92/07611 filed on Sep. 9, 1992 or a combination of both procedures. In particular, the dried particles are heated for a time sufficient to increase the modulus, centrifuge capacity, and/or the absorbency under load. Such heat-treatment is preferably carried out at a temperature of at least 170° C., more preferably of at least 180° C., and most preferably of at least 190° C. Such heat-treatment is preferably carried out at a temperature of less than 250° C., more preferably less than 240° C.

The time period for heat-treatment should be sufficient to effect an improvement in absorptive properties. The exact times of heat-treatment required will be affected by the equipment chosen, and can be determined empirically by examination of product properties. Preferably, the time is at least 3 minutes, and more preferably at least 5 minutes. If the time is too long, the process becomes uneconomical and a risk is run that the absorbent resin may be damaged. Preferably, the maximum time of heating is 150 minutes or less, more preferably 60 minutes or less.

The method of heat-treatment is not critical. For example, forced-air ovens, fluidized bed heaters, heated screw conveyors, and plate dryers, may be successfully employed. Other means of improving the absorptive properties of the dried particles include the known surface post-cross-linking technologies, processes which also incorporate heat-treatment in order to allow the surface post-cross-linking reaction to occur. These processes may also result in products which need remoisturization. The process of this invention is suitable to remoisturize this type of product.

The dried and heat-treated particles and the aqueous additive solution should be contacted under conditions such that the particles are being mixed (in motion) when the aqueous solution is added to assure good solution distribution and to minimize the risk of undesired or irreversible agglomeration. The risk of undesired or irreversible agglomeration disappears when the water is sufficiently migrated into the particles so that the surface again loses stickiness. Preferably, such remoisturization will be conducted with some form of mechanical distribution, such that adequate distribution of the aqueous additive solution on the water-absorbent resin particles occurs. Examples of blending equipment/processes include simple tumbling of a jar, or blending in a twin shaft paddle blender, ribbon blender, rotary blenders or high speed blenders, such as for example those available from NIRO A/S, Denmark. Moderate stirring, shaking, or even a short distance of conveying in a screw-conveyer can be sufficient for such adequate distribution of the aqueous additive solution over the particles, particularly if the particles are at an elevated temperature.

The temperature of contacting can be any temperature at which the aqueous additive solution does not significantly react with the carboxyl moieties or the cross-links of the superabsorbent polymer or evaporate. Such temperatures are typically at least from 20° C. to 100° C. at ambient pressure. It should be noted that elevated temperatures, that is, those above ambient temperatures, typically improve the speed of coating of the particles.

Another embodiment of the present invention comprises contacting the saline additive solution containing surface treatment additives before the heat-treatment. In order to achieve a more homogeneous distribution of cross-linkers or other surface treatment additives, the presence of additives like salt in the coating solution supports the more homogeneous distribution of the surface treatment additives on the surface of the superabsorbent polymer particles.

Suitable additives for the surface treatment of superabsorbent polymers according to the present invention include cross-linking agents, such as di- or polyfunctional agents that are capable of building additional cross-links between the polymer chains of the superabsorbent polymer. Other cross-linking agents include, for example, di- or polyhydric alcohols, or derivatives thereof which are capable of forming di- or polyhydric alcohols. Representatives of such agents are alkylene carbonates, ketales, and di- or polyglycidylethers. Typically, such additives are employed in amounts of from 100 to 50,000 ppm, based on dry powder, preferably between 500 and 10,000 ppm based on dry powder.

It will be readily understood that the surface treated polymer as described above will then be heat-treated according to the general teachings described above. After such heat-treatment, the superabsorbent may have varying levels of moisture. If the moisture level is below the desired level, the superabsorbent polymer can be subjected to the above-described post-remoisturization process without the use of the additive solution.

The following examples are provided for the purpose of explanation rather than limitation. The water-swellable polymer samples are standard commercially available materials. The actual composition of these materials is not relevant to the present invention, that is, the invention would be expected to be applicable to any commercially available water-swellable polymer materials.

EXAMPLES

A) Test Methods

Compaction Test 1

About 15 g of the product as obtained from a blender, as specified in the following examples, was placed in a metal cylinder, having a diameter of 2.6 cm and a height of 5 cm, and equipped with a polytetrafluoroethylene-coated piston having a weight of 365 g (6.8 kPa). The product was kept in the cylinder under pressure for 60 minutes and then carefully removed. It was checked visually whether or not the product compacted under the applied conditions, and if, whether the compacted block would disintegrate on shear and how easily. The ratings given were a) very stable, meaning that an irreversible agglomeration occurred; b) slightly brittle, meaning a considerable agglomeration partly irreversible; and c) brittle, meaning agglomeration that was easily disintegrated.

Compaction Test 2

The cohesiveness of some blends was reported in terms of a "Rathole Index". This was a standard test performed on a machine called Hang-up Indicizer, from J.R. Johanson Inc., in which a sample was compacted, and the force needed to break the compact was measured. The force was then converted to an estimated diameter of self-supporting hole that would develop in a hopper during funnel flow (a rathole). A satisfactory lack of cohesion was defined of having a rathole index of less than the diameter of the hopper discharge.

B) Experimental Procedure 1

Examples 1–6 and Comparative Example A
(Batch Remoisturization in the Lab Niro Blender)

Two kilograms (kg) of superabsorbent polymer resin having a moisture content (as determined by weight loss at 105° C. for 3 hours) of 0.1 to 2.5 percent were filled into the lab blender (type: P-K Blend Master, supplied by Niro A/S, Denmark) at ambient conditions. Both, the intensifier bar drive (high speed rotor) and the low speed shell drive (V-shaped housing drive) were switched on to assure best possible mixing during water addition. Hereafter, the water or the mixture of water and additives in the desired quantity and ratio were fed to the blender over a time period of about one minute. Both rotors were allowed to rotate and mix for one additional minute.

Thereafter, the intensifier bar drive was switched off, while the shell kept rotating for an additional 20 minutes, to assure sufficient residence time. Normally, due to loose agglomerates forming during or right after water addition, the bulk density of the product dropped so that the whole available volume in the shell was filled by expansion. This was associated with a loss of product flowability, so that only a minor fraction of the product could get in contact with the intensifier bar to be disintegrated. The shear forces applied to the product by shell rotation were in almost all cases too low to break even loose agglomerates which were formed. The product was removed from the blender and sieved over a set of sieves having openings of 10, 3 and 1 millimeters (mm) to separate coarse agglomerates from the non-agglomerated product. The fraction which passed the 1 mm sieve was analyzed by the standard particle size distribution analysis method. From the data obtained, the fraction with a particle size above 0.8 mm was calculated.

For Examples 1 through 6, and Comparative Example A, the feed polymer 1 (heat-treated, dry SAP, commercially available under the trade name XZ 95889.01 from Dow Deutschland Inc.) was treated according to the Experimental Procedure 1 with the types and amounts of additives as indicated in Table II. The resultant polymer particles were then tested for their absorptive characteristics and the results are also reported in Table I.

TABLE I

Influence of Additives on Agglomerate Formation and Agglomerate Stability.

| Example No. | Water (%) | Brine (%) (20% NaCl) | VORANOL * (ppm) | Agglomerates (% >0.8 mm) | Agglomerates Stability[1] | CC (g/g) | AUL (0.3 psi) (g/g) | AUL (0.6 psi) (g/g) | AUL (1.0 psi) (g/g) |
|---|---|---|---|---|---|---|---|---|---|
| Feed Polymer 1 | | | | | | 33.0 | 28.4 | 21.5 | 9.5 |
| Comp. Ex. A | 2 | — | — | 14.7 | very stable | | 28.5 | 17.2 | 10.0 |
| 1 | — | 2.5 | — | 23.5 | brittle | 32.6 | 28.6 | 20.1 | 9.2 |
| 2 | — | 4.5 | — | 95.5 | slightly brittle | 33.8 | n.d.[2] | 20.0 | n.d. |
| 3 | 4.0 | — | 1500 | 43.2 | brittle | 31.4 | n.d. | 21.7 | n.d. |
| 4 | — | 4.5 | 1500 | 19.8 | brittle | 31.1 | n.d. | 20.6 | n.d. |
| 5 | 6.0 | — | 1500 | 89.1 | brittle | 30.7 | n.d. | 21.0 | n.d. |
| 6 | — | 7.5 | 1500 | 39.7 | brittle | 30.8 | n.d. | 0.1 | n.d. |

*Trademark of The Dow Chemical Company
[1]Determined by applying compaction test 1
[2]n.d. = not determined The results of Examples 1 through 6 demonstrate the positive effect of the additives and of combinations of them on reducing agglomeration during remoisturization and on increasing the brittleness of the agglomerates. There were still fairly high levels of agglomeration obtained, however, agglomerates described as brittle in Table I would fairly easily disintegrate in a blender which could apply more shear to the product during residence time.

Moreover, as apparent from Example 2, the use of brine (NaCl) instead of pure water (Comp. Example A) increased the brittleness of the agglomerates which were formed and made them disintegratable. In the presence of other additives, such as VORANOL 2070, the level of agglomeration was reduced. The Centrifuged Capacity (CC) of the product was slightly reduced by the treatment; this was believed to be due to the natural "dilution effect." CC was determined with the product in its final composition. If a part of this final composition consisted of inert (non-swellable) water, then the absorption capacity of the "diluted" polymer was expected to be reduced.

Examples 7 through 9

The samples of the Examples 7 through 9 were produced in accordance with the Experimental Procedure 1, except for using feed polymer 2, 5500 ppm of highly ethoxylated trimethylolpropane triacrylate (HE-TMPTA) with a neutralization degree of 68 percent and which had not been heat-treated and had a moisture concentration of 2.5 percent. The types and amounts of additives are indicated in Table II. The resultant polymer particles were then tested for their absorptive characteristics and the results are also reported in Table II.

TABLE II

The Impact of Aluminum Chloride and Sodium Chloride on Agglomerate Formation and Absorption Performance

| Example No. | Water (%) | Brine (%) (20% NaCl) | AlCl$_3$ 6H$_2$O (ppm) | Agglomerates (% >0.8 mm) | CC (g/g) | AUL (0.3 psi) (g/g) | AUL (0.6 psi) (g/g) | AUL (1.0 psi) (g/g) |
|---|---|---|---|---|---|---|---|---|
| Feed Polymer 2 | | | | | 29.7 | 20.7 | 9.4 | 8.0 |
| 7 | 5 | — | 1000 | 63.7 | 27.6 | 25.5 | 17.4 | 9.3 |
| 8 | — | 6.25 | 1000 | 18.4 | 27.3 | 24.5 | 16.4 | 9.2 |
| 9 | — | 3.125 | 2000 | 7.4 | 24.8 | 24.0 | 18.8 | 11.4 |

The results of the Examples 7, 8 and 9 confirm the positive effect of NaCl and the strong impact of aluminum ions on reducing agglomeration. Aluminum ions also increased the absorption capabilities of the product under load, however, at the cost of Centrifuged Capacity reductions.

Experimental Procedure 2

The specific properties of the feed polymers for the trials 10 to 13 were not determined as no samples of the untreated heat-treated polymers were taken. The results therefore can only be compared with the comparative products Comp. Ex. B, C), which were obtained directly from a commercial production site after the experiments. They refer to the same feed polymer but were remoisturized in the production site by the standard method (0.7 percent pure water).

Examples 10 and 11
(Continuous Remoisturization on Industrial Scale)

Following the Experimental Procedure 2, the Examples 10 and 11 were performed with feed polymers 3 (same composition as feed polymer 2 but from a different production lot and which had been heat-treated) which had a CC of 28 g/g. The examples were performed in a blender (type 350 mm Zig-Zag Blender, supplied by Niro ANS, Denmark) which was connected with feeding lines for feed polymer and aqueous solutions. The feed polymer was charged into the blender at a rate of 1100±100 kg/hour, corresponding with a product residence time of one minute, and the liquid stream as required to obtain the desired degree of moisture in the product. Both feed streams were computer controlled. The blender discharges the moisturized product into a double screw conveyor (Segler SD 350), which provided sufficient working volume to assure additional residence time of 20 to 30 minutes under continuous mixing, thereby giving the water sufficient time to get distributed between and within the resin particles and to avoid agglomeration. After leaving this conveyor the remoisturized product was fed into a silo. Product samples were taken between the blender and the conveyor and in the line between the conveyor and the silo.

Examples 12 and 13 and Comparative Examples B and C

Following the procedure for Example 10, Examples 12, 13 and Comp. Ex. B and C were performed with feed polymers 4 and 5 which have a CC of 35 g/g and 29 g/g, respectively. Feed polymer 4 was a 3500 ppm of heat-treated HE-TMPTA with a neutralization degree of 68 percent and feed polymer 5 was a 5500 ppm of heat-treated HE-TMPTA with a neutralization degree of 68 percent. Results are given in Table III.

TABLE III

Continuous Remoisturization in a Production Scale High Speed Blender

| Example/ Comp. No. | Water (%) | Brine (%) (20% NaCl) | VORANOL (ppm) | Two Screw Conveyor | Agglomerates (% >0.8 mm) | CC (g/g) | AUL (0.3 psi) (g/g) | AUL (0.6 psi) (g/g) | AUL (1.0 psi) (g/g) |
|---|---|---|---|---|---|---|---|---|---|
| 10 | — | 2.5 | 500 | no | n.d.[1] | 28.1 | 28.2 | 22.3 | 17.5 |
| 11 | — | 2.5 | 500 | yes | 0.2 | 27.5 | 28.3 | 23.2 | 17.0 |
| C | 0.7 | — | — | yes | 1.4 | 28.8 | 28.5 | 22.9 | 17.3 |
| 12 | 2.0 | — | 500 | yes | 0.5 | 35.3 | 30.5 | 19.5 | 11.6 |
| 13 | — | 3.4 | 500 | yes | 1.1 | 30.4 | 29.1 | 21.9 | 15.6 |
| B | 0.7 | — | — | yes | 1.8 | 34.2 | 32.4 | 23.9 | 12.1 |

[1]The product as it left the blender was slightly wet and formed a very brittle block in the sample beaker. Reliable PSD measurement was not possible. Without additional residence time under permanent mixing this product would form a non-flowing block in a silo.

The results of Examples 10 through 13 confirm the importance of the additives in the remoisturization process. Examples 11 and 12 underline the importance of having sufficient residence time for the remoisturized resin in a mixer to prevent agglomeration until the water migrated away from the surface area into the cores of the resin particles and the reference samples, treated with only 0.7 percent water, no additives, show already significant agglomeration, and the agglomerates were not brittle.

Experimental Procedure 3

Examples 14 through 20
(Batch Remoisturization in the Forberg Style Paddle Blender)

1650 g of feed polymer 3 were placed into a Forberg blender and heated up to 50° C. prior to liquid addition. Aqueous solutions containing the various additives were sprayed onto the polymer material using an atomizing spray nozzle. The solutions were applied in one gram of water per 100 grams of SAP aliquots, and the mixture was agitated four minutes after each aliquot. After the desired amount of liquid was added, the polymer was removed from the blender.

Table IV summarizes results of Examples 14 through 20. In these runs, the Experimental Procedure 3 was applied for the remoisturization of the feed polymer 6. Feed polymer 6 was a dry, heat-treated, partially neutralized polyacrylic acid containing highly ethoxylated trimethylolpropane triacrylate as the primary cross-linking agent and polyethylene glycol as the secondary cross-linking agent.

TABLE IV

Remoisturization of SAP with various Additives in a Forberg Blender (all concentrations are based on solid feed polymer)

| Example # | Feed polymer 6 | 14 | 15 | 16 | 17 | 18 | 19 | 20 |
|---|---|---|---|---|---|---|---|---|
| Polyol (ppm) | — | 650 | 1950 | 650 | 650 | — | — | — |
| NaCl. (ppm) | — | — | — | — | 10400 | — | — | — |
| $Na_2SO_4$ (ppm) | — | — | — | 10500 | — | — | — | — |
| $AL^{3+}$ (ppm) | — | — | — | — | — | 540 | 1270 | 2120 |
| CC (g/g) | 36.5 | 34.1 | | | | 32.8 | 31.4 | 32.1 |
| $AUL_{0.3psi}$ (g/g) | 33.7 | 29.6 | | | | 27.5 | 25.6 | 25.3 |
| $AUL_{0.6psi}$ (g/g) | 21.5 | 18.1 | | | | 16.9 | 14.7 | 15.7 |
| $AUL_{0.9psi}$ (g/g) | 12.7 | 11.9 | | | | 11.2 | 11.5 | 10.3 |
| Moisture content (%) at which the Rathole Index of 30.48 cm (1 ft) is exceeded | 2 | 4 | 4 | 6 | 4 | 5 | 6 | >10 |

These data show that aluminum sulfate and sodium sulfate can suppress the cohesiveness of wetted resin particles as measured using the Indicizer. It appeared that the polyol allowed the water to be more evenly distributed over the surface of the resin particles allowing twice as much water to be applied before the particles begin to agglomerate. These data also indicated an additive effect using the salts which further reduced the cohesiveness of the resin particles. Depending on the type and amount of added salt, the data showed that the resin can absorb greater than 10 percent of its mass in water without becoming cohesive.

Experimental Procedure 4

Examples 21 through 24
(Continuous Remoisturization in the Munson Blender)

These examples employ feed polymer 7 which was a dry, heat-treated, partially neutralized polyacrylic acid containing trimethylolpropane triacrylate as the primary cross-linking agent and polyethylene glycol as the secondary cross-linking agent. Feed polymer 7 was continuously charged into the Munson blender, type 1 6×4, with a feed rate of 4.536 kg/minute by the aid of a screw feeder. This continuous blender was equipped with four 4.45 cm wide metal strips bent in a saw tooth pattern positioned 90 degrees apart having a "wavelength" of 23.5 cm and a bend-to-bend length of 16.2 cm. Lifters were fixed to the cylinder wall, and the entire cylinder rotated at a rate of 15 rpm. An internal weir of 7.94 cm height assures a retention volume of 26.3 liters and a residence time under the given feed rate of 4 minutes. The spray nozzles of the types small and large hydraulic nozzles (models 650017 and 650067) were supplied by Spraying Systems Company. Samples were taken at steady state conditions (after 12 minutes operation time).

Feed polymer 7 was treated according to the Experimental Procedure 4 in the continuous Munson blender. In Examples 21 through 24, the source of aluminum was hydrated aluminum sulfate. Conditions and results were given in Table V.

TABLE V

Remoisturization of SAP under various Conditions in a Continuously operating Munson Blender

| Example # | 21 | 22 | 23 | 24 |
|---|---|---|---|---|
| Added Moisture (%, b.o. wet) | 1.33 | 1.79 | 1.84 | 1.86 |
| Liquid Flow Rate (ml/min.) | 61 | 85.7 | 87 | 90.4 |
| Polyol (ppm, b.o. dry) | 0 | 630 | 0 | 650 |
| $Al^{3+}$ (ppm, b.o. dry) | 0 | 0 | 985 | 1000 |

TABLE V-continued

Remoisturization of SAP under various Conditions in a Continuously operating Munson Blender

| Example # | 21 | 22 | 23 | 24 |
|---|---|---|---|---|
| Oversize (greater than 800 micron, %) | 1.05 | 0.02 | 0.02 | 0 |
| CC (g/g) | 25.3 | 27.1 | 27.9 | 28.4 |
| $AUL_{0.3\ psi}$ (g/g) | 28.2 | 28.1 | 27.7 | 27.1 |
| $AUL_{0.6\ psi}$ (g/g) | 23.3 | 24.6 | 22.4 | 20.6 |
| $AUL_{0.9\ psi}$ (g/g) | 18.1 | 19.5 | 17.2 | 13.6 |

The data in Table V again show how the polyol and the aluminum sulfate suppress the cohesiveness of wetted resin particles. Each of the additives used separately performed similarly in this experiment. However, when used together, as in Example 24, no resin agglomeration was detectable at these moisture addition levels. This was a significant improvement over the level of agglomerate formation caused by adding water without the additives (Example 21).

Experimental Procedure 5

Examples 25 and 26

Improved Distribution of Reactants on the Surface of SAP Particles

For these Examples, feed polymer 8, a non-heat-treated SAP cross-linked with 4000 ppm of HE-TMPTA, 68 percent neutralized, was employed. 50 g of SAP and 3.75 g of water in which the desired additives were solved were mixed in a 300 mL glass beaker with the aid of a spatula. Using this operation some fairly brittle agglomerates were formed. 10 minutes after mixing, these agglomerates were broken by carefully pushing the product through a 1 mm screen.

Successively, 20 g of the coated material was subjected to heat-treatment in the lab fluidized bed drier at 200° C. for 15 min. The results were given in Table VI.

TABLE VI

The Effect of Metal Ions on the Distribution of Reactants in Solution on the SAP Surface.

| Example | Feed Polymer 8 | 25 | 26 |
|---|---|---|---|
| Water (% based on solid) | | 7.5 | 7.5 |
| GAPE[1] (ppm, based on solid) | | 1000 | 1000 |
| DOWANOL*-TPM (%, based on solid) | | 1.5 | 1.5 |
| NaCl (%, based on solid) | | 0 | 1.5 |
| CC (g/g) | 36.3 | 39.8 | 37.3 |
| $AUL_{0.6\ psi}$ (g/g) | 7.7 | 21.3 | 25.5 |
| $AUL_{1.0\ psi}$ (g/g) | 8.0 | 10.4 | 13 |

[1]GAPE = gallic acid propyl ester
*Trademark of The Dow Chemical Company

From the teachings of WO95/05856 it was known that the presence of inhibitors supports the buildup of AUL during heat-treatment of superabsorbent polymers. The results of Experiments 25 and 26 prove that the presence of salt in the aqueous inhibitor solution allowed a more homogeneous distribution of the inhibitor solution on the particles surface and provides such an increased AUL buildup without the use of hydrophilic solvents and/or surfactants.

Experimental Procedure 6

Examples 27 to 30

Improved Distribution of Surface Post-Cross-linking Agents on the Surface of SAP Particles For these examples feed polymer 9, a heat-treated SAP cross-linked with 4300 ppm of HE-TMPTA, 68 percent neutralized was employed. 50 g of the feed polymer were placed into a flat tray of a diameter of 20 cm in the form of a thin layer. An aqueous solution containing 6.97 percent of glycerin, Experiments 27 and 29, and 5.66 percent glycerin and 18.87 percent of sodium chloride, Experiments 28 and 30, was sprayed onto the product and further manually mixed until the solution was distributed as homogeneously as possible. The solutions were added to the polymers until they contained 3000 ppm of glycerin and 4 percent of water, based on feed polymer.

Loose agglomerates which were formed by this operation were substantially disintegrated by sweeping the mixed product through an 800 micron sieve. Successively, 20 g portions of the coated product were subjected to heat-treatment in a lab fluidized bed drier at 200° C. for 5 minutes, Experiments 27 and 28, and for 10 minutes, experiments 29 and 30. To completely disintegrate residual agglomerates, the heat-treated product was again swept through a 0.8 micron sieve. The heat-treatment times and the results were given in Table VII.

TABLE VII

The Effect of Metal Ions on the Distribution of Surface-Cross-linker on the SAP Surface

| Example | Feed polymer 8 | 27 | 28 | 29 | 30 |
|---|---|---|---|---|---|
| Water (% based on solid) | — | 4 | 4 | 4 | 4 |
| NaCl (%, based on solid) | — | — | 1 | — | 1 |
| Glycerin (ppm based on solid) | — | 3000 | 3000 | 3000 | 3000 |
| Heat-Treatment (min) | — | 5 | 5 | 10 | 10 |
| CC (g/g) | 41.3 | 36.0 | 31.3 | 31.5 | 29.9 |
| $AUL_{0.3\ psi}$ (g/g) | 10.2 | 26.0 | 27.3 | 29.1 | 26.2 |
| $AUL_{0.6\ psi}$ (g/g) | 7.3 | 18.7 | 20.5 | 21.1 | 21.2 |
| $AUL_{0.9\ psi}$ (g/g) | 4.4 | 11.9 | 17.4 | 15.4 | 18.1 |

The results show that the presence of metal salts in the coating formulation improved the distribution of the surface post-cross-linker on the surface of the SAP particles. Optimal distribution of the post cross-linker was essential for the formation of a homogeneous shell of higher cross-link density round the particles and hence, better distribution supports the desired buildup of a high AUL. Surprisingly, if the coating solution contained metal salts, there was no need for hydrophilic organic solvents, water insoluble, or inorganic salts, or surfactants.

What is claimed is:

1. A composition comprising aqueous fluid absorbent polymer particles which have been heat-treated at temperatures greater than 170° C. for more than 10 minutes, wherein the composition has been remoisturized, after the heat-treatment, with an aqueous additive solution containing a mono- or multivalent metal salt, in the absence of an organic solvent or water-insoluble, non-swellable powder, and wherein the composition comprises 1 to 10 percent by weight, based on the total weight of the composition, water and wherein the composition is characterized by the ability to absorb at least 20 grams of a 0.9 weight percent aqueous saline solution under a pressure of 0.3 psi (21,000 dynes/$cm^2$), that is, a 60 minute 0.3 psi (21,000 dynes/$cm^2$) AUL greater than 20 grams/gram.

2. Composition according to claim 1 characterized in that the aqueous additive solution contains monovalent metal salt.

3. Composition according to claim 1 characterized in that the aqueous additive solution is a 1 to 40 percent KCl or NaCl solution.

4. Composition according to claim 1 characterized in that the aqueous additive solution is a 20 percent NaCl solution.

5. Composition according to claim 1 characterized in that the monovalent metal salt is employed in an amount of from 0.05 to 5 percent, based on the total SAP.

6. Composition according to claim 1 characterized in that the aqueous additive solution containing a mono- or multivalent metal salt further comprises a propoxylated polyol.

7. Composition according to claim 1 characterized in that the aqueous additive solution contains a sulfate-based metal salt.

8. Composition according to claim 1 characterized in that the aqueous additive solution contains aluminum sulfate, aluminum chloride, sodium chloride or sodium sulfate.

9. Composition according to claim 7 characterized in that the aqueous additive solution contains sodium sulfate.

10. Composition according to claim 8 characterized in that the aqueous additive solution contains aluminum sulfate.

11. Composition according to claim 1 characterized in that it comprises between 1 and 6 percent water.

12. Composition according to claim 1 characterized in that the multivalent metal cation is employed in an amount of 500 to 5,000 ppm, based on total weight of dry SAP.

13. Composition according to claim 12 characterized in that multivalent metal cation is employed in an amount of 1,000 to 2,500 ppm, based on the total weight of dry SAP.

14. A process comprising:
   (a) preparing a water-swellable hydrogel by a gel polymerization process;
   (b) drying and sizing the hydrogel to form a composition comprising dried and sized particles, the composition comprising particles having a particle size distribution of 50 to 1500 microns;
   (c) heat-treatment; and
   (d) contacting the composition with an aqueous additive solution containing a mono- or multivalent metal salt in the absence of an organic solvent or water-insoluble inorganic powders, wherein the composition is characterized by a 60 minute 0.3 psi (21,000 dynes/cm2) AUL greater than 20 grams/gram.

15. A superabsorbent polymer prepared by:
   (a) gel polymerizing a monomer mixture into a water-swellable hydrogel;
   (b) drying and sizing the hydrogel to form a composition comprising dried and sized particles, the composition comprising particles having a particle size distribution of 50 to 1500 microns;
   (c) heat-treating the resultant composition; and
   (d) contacting the composition with an aqueous additive solution containing a mono- or multivalent metal salt in the absence of an organic solvent or water-insoluble inorganic powders, wherein the composition is characterized by a 60 minute 0.3 psi (21,000 dynes/cm$^2$) AUL greater than 20 grams/gram.

16. A process comprising:
   (a) preparing a water-swellable hydrogel by a gel polymerization process;
   (b) drying and sizing the hydrogel to form a composition comprising dried and sized particles, the composition comprising particles having a particle size distribution of 50 to 1500 microns;
   (c) contacting the composition with an aqueous additive solution containing a mono- or multivalent metal salt in the absence of an organic solvent or water-insoluble inorganic powders, wherein the composition is characterized by a 60 minute 0.3 psi (21,000 dynes/cm$^2$) AUL greater than 20 grams/gram;
   (d) drying and/or heat-treating the composition; and optionally,
   (e) remoisturization of the heat-treated SAP so that the resultant SAP contains up to 10 percent of water.

17. The process according to claim 16 characterized in that the additive solution is a solution further comprising cross-linkers.

18. The process according to claim 17 characterized in that the cross-linker is a bi- or polyfunctional agent capable of building additional cross-links between the polymer chains of the SAP.

19. Composition according to claim 2 characterized in that the aqueous additive solution is a 20 percent NaCl solution.

20. Composition according to claim 3 characterized in that the aqueous additive solution is a 20 percent NaCl solution.

21. Composition according to claim 2 characterized in that the monovalent metal salt is employed in an amount of from 0.05 to 5 percent, based on the total SAP.

22. Composition according to claim 3 characterized in that the monovalent metal salt is employed in an amount of from 0.05 to 5 percent, based on the total SAP.

* * * * *